United States Patent
Gleich et al.

(10) Patent No.: US 8,044,660 B2
(45) Date of Patent: Oct. 25, 2011

(54) ARRANGEMENT AND METHOD FOR INFLUENCING AND/OR DETECTING MAGNETIC PARTICLES IN A REGION OF ACTION

(75) Inventors: Bernhard Gleich, Hamburg (DE); Juergen Weizenecker, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 201 days.

(21) Appl. No.: 12/519,775

(22) PCT Filed: Dec. 14, 2007

(86) PCT No.: PCT/IB2007/055131
§ 371 (c)(1),
(2), (4) Date: Jun. 18, 2009

(87) PCT Pub. No.: WO2008/078244
PCT Pub. Date: Jul. 3, 2008

(65) Prior Publication Data
US 2010/0033174 A1    Feb. 11, 2010

(30) Foreign Application Priority Data
Dec. 20, 2006 (EP) ................................. 06126579

(51) Int. Cl.
*G01N 27/72* (2006.01)
*G01R 35/00* (2006.01)

(52) U.S. Cl. ....................................... 324/228; 324/202
(58) Field of Classification Search .................. 324/202, 324/228; 600/12; 128/899
See application file for complete search history.

(56) References Cited

U.S. PATENT DOCUMENTS
6,501,274 B1    12/2002    Ledden

FOREIGN PATENT DOCUMENTS

| DE | 10151778 | 5/2003 |
|---|---|---|
| EP | 1304542 | 4/2003 |
| WO | WO2004091392 | 10/2004 |
| WO | WO2006035359 | 4/2006 |
| WO | WO2006064405 | 6/2006 |

*Primary Examiner* — Bot Ledynh

(57) ABSTRACT

An arrangement for influencing and/or detecting magnetic particles, and/or calibrating such an arrangement includes generating a magnetic selection field having a magnetic field strength pattern such that a first sub-zone having a low magnetic field strength and a second sub-zone having a higher magnetic field strength are formed in the region of action. A driver changes the position in space of the two sub-zones in the region of action by magnetic drive field so that the magnetization of the magnetic particles changes locally. The arrangement includes a drive signal chain, a detection signal chain, and a receiver for acquiring detection signals that depend on the magnetization in the region of action. The magnetization is influenced by the change in the position in space of the first and second sub-zones. A compensation controller provides a compensation signal to the drive signal chain and/or to the detection signal chain by a coupler.

14 Claims, 5 Drawing Sheets

ARRANGEMENT AND METHOD FOR INFLUENCING AND/OR DETECTING MAGNETIC PARTICLES IN A REGION OF ACTION

CROSS REFERENCE TO RELATED APPLICATIONS

This application claims the benefit of EP provisional application s/n 06126581.5, filed Dec. 20, 2006, which is incorporated herein by reference. Related applications are PCT s/n IB2007/055126, "Arrangement and Method for Influencing and/or Detecting Magnetic Particles in a Region of Action," filed Dec. 14, 2007, PCT s/n IB2007/055152, "Arrangement for Influencing and/or Detecting Magnetic Particles in a Region of Action and Method of Producing a Disk Shaped Coil," filed Dec. 17, 2007, PCT s/n IB2007/055157, "Arrangement and Method for Influencing and/or Detecting Magnetic Particles in a Region of Action," filed Dec. 17, 2007, PCT s/n IB2007/055134, "Arrangement and Method for Influencing and/or Detecting Magnetic Particles in a Region of Action," filed Dec. 14, 2007, PCT s/n IB2007/055174, "Arrangement and Method for Influencing and/or Detecting Magnetic Particles in a Region of Action," filed Dec. 17, 2007, PCT s/n IB2007/055158, "Arrangement and Method for Influencing and/or Detecting and/or Locating Magnetic Particles in a Region of Action," filed Dec. 17, 2007, PCT s/n IB2007/055162, "Method and Arrangement for Locating Magnetic Markers in a Region of Action," filed Dec. 17, 2007, PCT s/n IB2007/055178, "Arrangement and Method for Detecting and/or Locating a Magnetic Material in a Region of Action, Use of a Arrangement In the Examination of Buildings," filed Dec. 17, 2007, PCT s/n IB2007/055177, "Method and Arrangement for Influencing and/or Detecting Magnetic Particles in a Region of Action," filed Dec. 17, 2007, PCT s/n IB2007/055204, "Method and Arrangement for Separating Magnetic Particles, Magnetic Particles and Use of Magnetic Particles," filed Dec. 18, 2007, PCT s/n IB2007/055165, "Arrangement and Method for Influencing and/or Detecting Magnetic Particles in a Region of Action, Coil Arrangement," filed Dec. 17, 2007, and PCT s/n IB2007/055163, "Influencing and/or Detecting Magnetic Particles in a Region of Action of a Examination Object," filed Dec. 17, 2007.

The present invention relates to an arrangement for influencing and/or detecting magnetic particles in a region of action. Furthermore, the invention relates to a method for influencing and/or detecting magnetic particles in a region of action and to a method for calibrating an arrangement according to the present invention.

The arrangement and the method of this kind is known from German patent application DE 101 51 778 A1. In the case of the method described in that publication, first of all a magnetic field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement and such a method have the advantage that it can be used to examine arbitrary examination objects—e.g. human bodies—in a non-destructive manner and without causing any damage and with a high spatial resolution, both close to the surface and remote from the surface of the examination object.

Known arrangements of this type have shown the disadvantage that the signal strength of the interesting signals measured or detected by the receiving means is very weak compared to the signals due to induction by the drive means and therefore signal detection is very complicated. The ratio of the amplitudes of the signals induced by the drive means and the interesting signals in the receiving means can reach ten orders of magnitude. The use of passive filter stages adds a lot to the costs of known arrangements; as usually high power is involved and usually high quality filters are needed, such known arrangements become bulky and expensive.

It is therefore an object of the present invention to provide an arrangement and a method of the kind mentioned initially, in which the signal detection is improved and/or the arrangement is less bulky and/or more cost effective.

The above object is achieved by an arrangement for influencing and/or detecting magnetic particles in a region of action, wherein the arrangement comprises selection means for generating a magnetic selection field having a pattern in space of its magnetic field strength such that a first sub-zone having a low magnetic field strength and a second sub-zone having a higher magnetic field strength are formed in the region of action, drive means for changing the position in space of the two sub-zones in the region of action by means of a magnetic drive field so that the magnetization of the magnetic particles changes locally, the arrangement comprising a drive signal chain, receiving means for acquiring detection signals, which detection signals depend on the magnetization in the region of action, which magnetization is influenced by the change in the position in space of the first and second sub-zone, the arrangement comprising a detection signal chain, wherein the arrangement comprises a compensation controller providing a compensation signal to the drive signal chain and/or to the detection signal chain by means of a coupling means.

The inventive arrangement according to the present invention has the advantage that it is possible to enhance the signal to noise ratio by means of using a compensation controller providing a compensation signal to the drive signal chain and/or to the detection signal chain by means of a coupling means. One of the signal detection problems occurring in an arrangement according to the present invention is the induced voltage in the receiving means (also called the recording means or recording system) due to the existence of the magnetic drive field. This induced voltage due to the presence of the magnetic drive field is typically much larger than the (useful and only interesting) signal voltage of the detection signal. The measurement principle of the arrangement according to the present invention relies on the fact that a magnetic drive field with a dedicated frequency influences the magnetic particles which send out a signal including this frequency but also higher harmonics. These harmonics are measured. Therefore, either the spectrum of the drive field itself must not contain higher harmonics of the dedicated frequency or the higher harmonics of the dedicated frequency have to be eliminated or compensated for—either in the so-called drive signal chain or in the so-called detection signal chain. Especially, it is preferred that the compensation signal is filtered prior to being coupled to the drive signal chain and/or to the detection signal chain. This provides the possibility to add the lowest possible portion of noise to the signals in the drive signal chain and/or the detection signal chain.

According to the present invention, several electronic means and methods to block the unwanted voltage or to compensate for the unwanted voltage are suggested. According to the present invention, a compensation controller is provided at the inventive arrangement such that a compensation signal is coupled to a drive signal chain and/or to a detection signal chain. In the context of the present invention, the term drive signal chain signifies the different stages—e.g. amplifying stage, filtering stage or the like—in order to generate the drive signal fed to the drive means. Likewise in the context of the present invention, the term detection signal chain signifies the different stages—e.g. amplifying stage, filtering stage or the like—in order to generate the detection signal received by the receiving means.

According to the present invention, it is to be understood that the selection means and/or the drive means and/or the receiving means can at least partially be provided in the form of one single coil or solenoid. However, it is preferred according to the present invention that separate coils are provided to form the selection means, the drive means and the receiving means. Furthermore according to the present invention, the selection means and/or the drive means and/or the receiving means can each be composed of separate individual parts, especially separate individual coils or solenoids, provided and/or arranged such that the separate parts form together the selection means and/or the drive means and/or the receiving means. Especially for the drive means and/or the selection means, a plurality of parts, especially pairs for coils (e.g. in a Helmholtz or Anti-Helmholtz configuration) are preferred in order to provide the possibility to generate and/or to detect components of magnetic fields directed in different spatial directions.

According to the present invention, several embodiments are suggested for realizing a compensation controller in connection with an inventive arrangement.

In a first embodiment according to the present invention, a compensation controller comprising passive electronics for the compensation of the unwanted voltages in the detection signal or detection signals is used. In this embodiment of the compensation controller, electronics signals from the drive means (especially magnetic drive field coils) are fed to the compensation controller. This can be done in an inductive and/or capacitive and/or resistive way. In addition or alternatively to the feeding of the electronics signals from the drive means, the uncompensated signals from the receiving means (also called recording coils) are fed to the compensation controller. The feeding of the electronics signals from the drive means and/or from the receiving means is also called a feedback signal from the drive signal chain or from the detection signal chain. The electronics of the compensation controller provides preferably a shifting of the phase and an adjustment of the amplitude of the reference signals (i.e. either the electronics signals from the drive means or the uncompensated signals from the receiving means or both of them) and couples them to the detection signals (also called recording signals) as a compensation signal. The coupling of the compensation signal to the detection signal chain is done in a way that only little noise is added to the high frequency components of the receiving means (or recording coil). In a further variant of the first embodiment, the compensation controller comprise passive and/or active elements for phase shifting and amplitude adjustments. These phase shifting and/or amplitude adjustments may be controlled by means of a computer.

In a second embodiment according to the present invention, the compensation controller comprises an electronic means providing a digital signal being converted to a voltage over time. This voltage is also called the compensation signal. As in the first embodiment according to the present invention, this compensation signal (or voltage over time) is coupled into the detection signal chain, i.e. into the signal from the recording coil, in order to compensate the signals induced inside the receiving means due to the magnetic drive field or fields. According to a variant of the second embodiment, it is possible that after the generation of the compensation signal, this signal travels trough a compensation signal chain in order to be filtered and/or amplified and/or modified or corrected in a further way. This is done, e.g., to reduce undesired frequency components and is similar to the treatment of the signal inside the drive signal chain. The coupling of the compensation signal to the detection signal chain (signals from the receiving coils) can be done, e.g., by a transformer (inductive coupling), i.e. similar as when using a (stationary and/or moveable) compensation coil as part of the receiving means. The digital generation of the compensation signal allows for more degrees of freedom allowing e.g. the realization of the coupling means by means of a capacitive bypass.

In a third embodiment according to the present invention, the compensation controller provides a compensation signal that is later subjected to a broad band signal chain (as a special embodiment of a compensation signal chain). The compensation signal is coupled or fed to the drive signal chain after having passed the broad band signal chain. This is done in a way that the higher harmonics in the signal of the drive signal chain (also called original signal chain) are precisely compensated. The feeding or coupling point is preferably not directly after the amplifier of the drive signal chain as in that case the needed power for the compensation signal chain or the broad band signal chain would be comparably high. According to variants of the third embodiment of the present invention, different coupling points are possible. Especially resistive coupling is used according to the third embodiment. According to further variants of the third embodiment of the present invention, the point of the coupling is preferably chosen such that at least one final passive filter stage is provided after the point of coupling of the compensation signal to the drive signal chain. This has the advantage that the performance of the inventive arrangement and especially the performance of the compensation is not limited by the precision of a control loop which is also called feedback loop. According to variants of the third embodiment of the present invention, the feedback loop can either be realized in a continuous (or dynamic) manner or in a calibration mode. In both variants of the inventive arrangement, a feedback signal is derived—at least indirectly—from the drive signal chain such that the higher harmonics can be measured therein. In the calibration mode, the inventive arrangement is e.g. provided without a sample inside the arrangement and at different power levels and frequencies of the drive signal the higher harmonics are measured. According to the present invention, this can be done using different measuring points at the coupling means as origins for the feedback signal. It is thereby possible to provide measurements of the calibration variations in the drive signals. Alternatively according to the third embodiment of the present invention and contrary to the calibration mode, it is possible that the feedback signal is provided in a feedback loop by means of an additional receiving means, i.e. especially an additional receiving coil. The additional receiving coil is preferably provided near the sample position and with a low sensitivity to the sample.

For all embodiments according to the present invention, it is advantageous that the compensation signal is coupled to the drive signal chain and/or to the detection signal chain by means of capacitive coupling and/or by means of resistive coupling and/or by means of inductive coupling, especially by means of a capacitive bypass. This has the advantage, that well-known coupling types can be used according to the present invention such that the inventive arrangement can be provided in a very cost efficient manner. Furthermore, it is especially preferred to use a capacitive coupling or an inductive coupling. This has the advantage that the coupling is done in a way that only little noise is added to the high frequency components of the receiving coil.

According to the present invention is particularly preferable that the compensation controller is provided with a feedback signal from the drive signal chain and/or from the detection signal chain. In the first embodiment, the example of a feedback signal originating from the drive signal chain and/or from the detection signal chain is given. In the third embodiment, the example of the feedback signal is given where the feedback signal is generated by means of an additional receiving means, i.e. especially an additional receiving coil. The generation of a feedback signal has generally the advantage that the inventive arrangement can be used in a self regulatory regime or in a self calibration mode. This means that changes in the behavior of one component of the inventive arrangement can be dynamically compensated for.

In a further variant of all of the embodiments, the compensation controller is controlled by a computer. Especially, the compensation controller comprises passive and/or active elements for phase shifting and amplitude adjustments. These phase shifting and/or amplitude adjustments and generally all the components of the compensation controller may be controlled by means of a computer. The use of a computer to control the compensation controller is advantageous because thereby a very adaptive behavior of the inventive arrangement in different application scenarios can be achieved and through the digital generation of the compensation signal it is possible to realize a greater number of degrees of freedom allowing e.g. the realization of the coupling means by means of a capacitive bypass.

The selection means and the drive means together are also called "field generator means". The selection means comprise magnetic field generation means that provide either a static (gradient) magnetic selection field and/or a comparably slowly changing long range magnetic selection field with frequencies in the range of about 1 Hz to about 100 Hz. Both the static part and the comparably slowly changing part of the magnetic selection field can be generated by means of a permanent magnet or by means of coils or by a combination thereof. The drive means comprise magnetic field generation means that provide a magnetic drive field with frequencies in the range of about 1 kHz to about 200 kHz, preferably about 10 kHz to about 100 kHz. At least part of the field generator means (i.e. the selection means and the drive means) can be implemented by discrete coils where the diameter of the current supporting path (or the individual wires in the case of litz wire) of each coil or of each field generator means has to be chosen in such a way that the skin effect does not increase the resistance of the coil.

The present invention further refers to a method of influencing and/or detecting magnetic particles in a region of action, wherein the method comprises the steps of generating a magnetic selection field having a pattern in space of its magnetic field strength such that a first sub-zone having a low magnetic field strength and a second sub-zone having a higher magnetic field strength are formed in the region of action, changing the position in space of the two sub-zones in the region of action by means of a magnetic drive field formed by drive signals so that the magnetization of the magnetic particles changes locally, acquiring detection signals, which detection signals depend on the magnetization in the region of action, which magnetization is influenced by the change in the position in space of the first and second sub-zone, compensating the drive signals and/or the detection signals by means of a compensation signal coupled to the drive signals and/or coupled to the detection signals.

The advantage of this method according to the present invention is that it is possible to influence and/or to detect magnetic particles by means of a much less bulky and expensive equipment. Furthermore, it is possible with the method according to the present invention to apply the compensation signal dynamically by means of a feedback signal. The feedback signal is e.g. provided in the form of measurements and/or in the form of signals provided by additional receiving means, which signals are related, e.g., to the drive signals.

The present invention further refers to a method for calibrating an arrangement for influencing and/or detecting magnetic particles in a region of action, wherein the method comprises the steps of generating a magnetic selection field having a pattern in space of its magnetic field strength such that a first sub-zone having a low magnetic field strength and a second sub-zone having a higher magnetic field strength are formed in the region of action, changing the position in space of the two sub-zones in the region of action by means of a magnetic drive field formed by drive signals, acquiring detection signals, which detection signals depend on the magnetic drive field and/or on the magnetization in the region of action, which magnetization is influenced by the change in the position in space of the first and second sub-zone, generating a compensation signal coupled to the drive signals and/or coupled to the detection signals by means of measuring calibration variations in the drive signal and/or in the detection signal or applying calibration variations of the compensation signal to the drive signals and/or to the detection signals and computing the compensation signal.

The advantage of this method according to the present invention is that it is possible to provide a stable yet flexible functioning of the arrangement by first calibrating the arrangement according to the method for calibrating and then using the method for influencing and/or detecting magnetic particles in a region of action.

According to the present invention, it is preferred that the calibration variation of the compensation signal are provided and/or measured as phase shift variations and/or amplitude variations. This provides the possibility of advantageously compensate for higher harmonics in a very efficient way.

Furthermore according to the present invention, it is preferred that the method comprises the steps of changing the position in space of the two sub-zones in the region of action by means of the magnetic drive field so that the magnetization of the magnetic particles changes locally. According to the present invention, it can be advantageous to first calibrate the inventive arrangement without magnetic particles positioned in the region of action.

According to a preferred embodiment of the present invention, the compensation signal is computed by means of applying linear theory calculations. This advantageously gives the possibility to comparably easily calculate the compensation signal necessary to apply in a given situation, e.g., by matrix inversion, where the single matrix elements comprise measurements of the effect of applying calibration variations of the compensation signal.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

Figure 6:
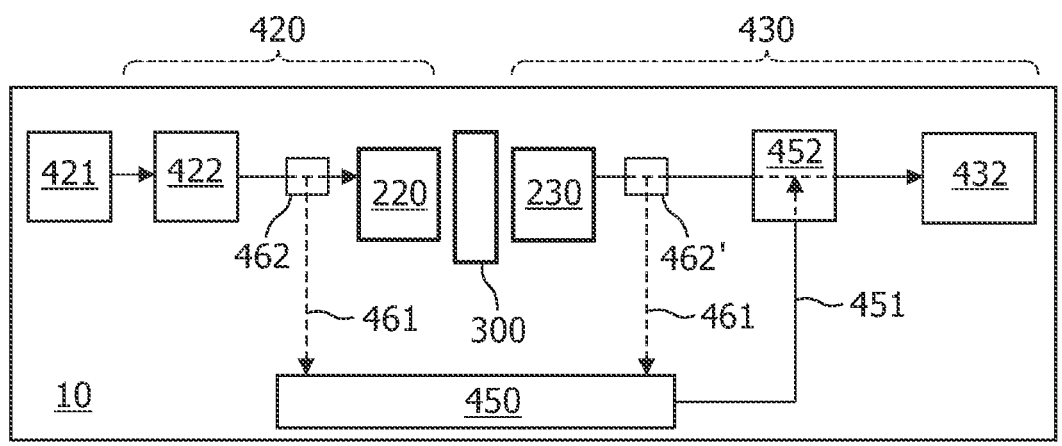
Figure 7:
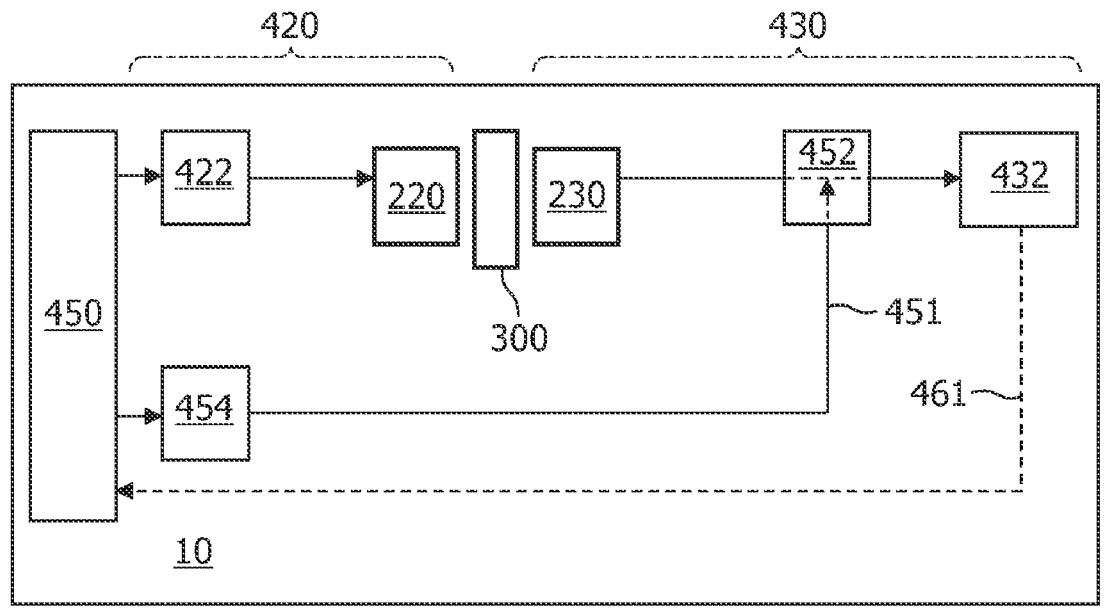
Figure 9:
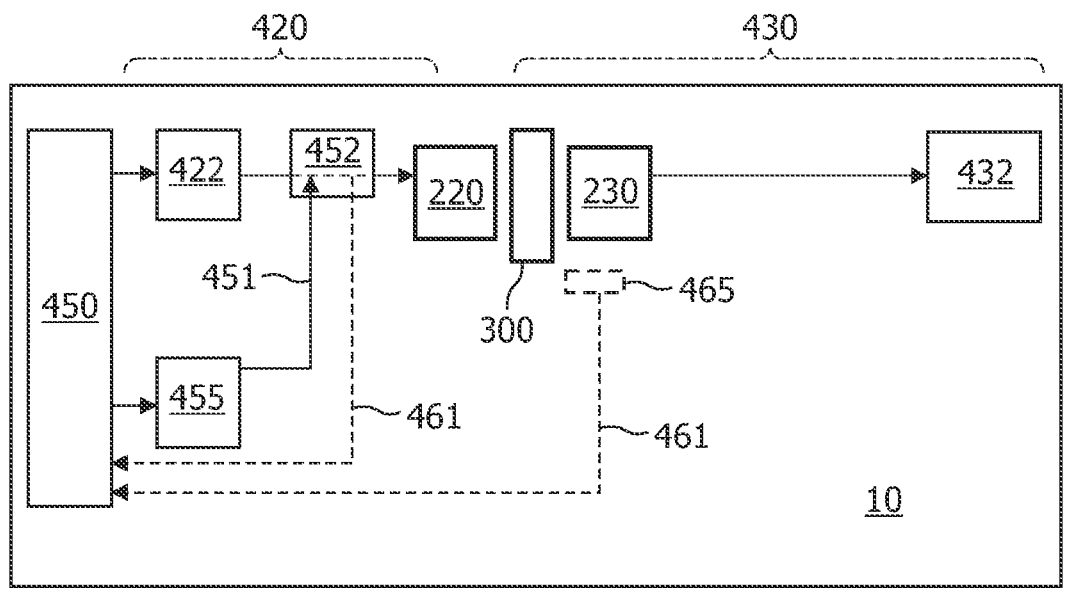

FIGS. 6, 7 and 9 schematically represent different embodiments of an arrangement 10 according to the present invention.

Figure 8:
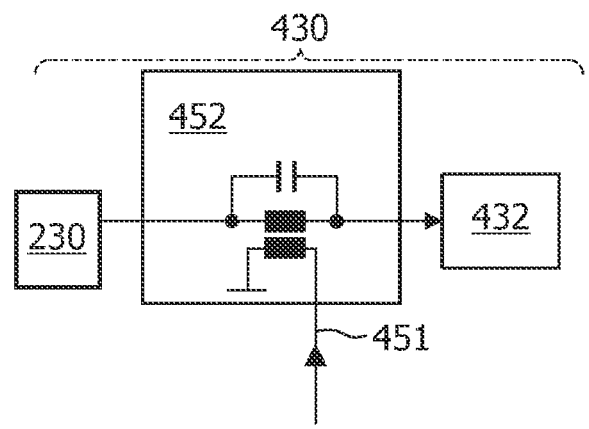

FIG. 8 schematically represents an embodiments of a detection signal chain.

Figure 10:
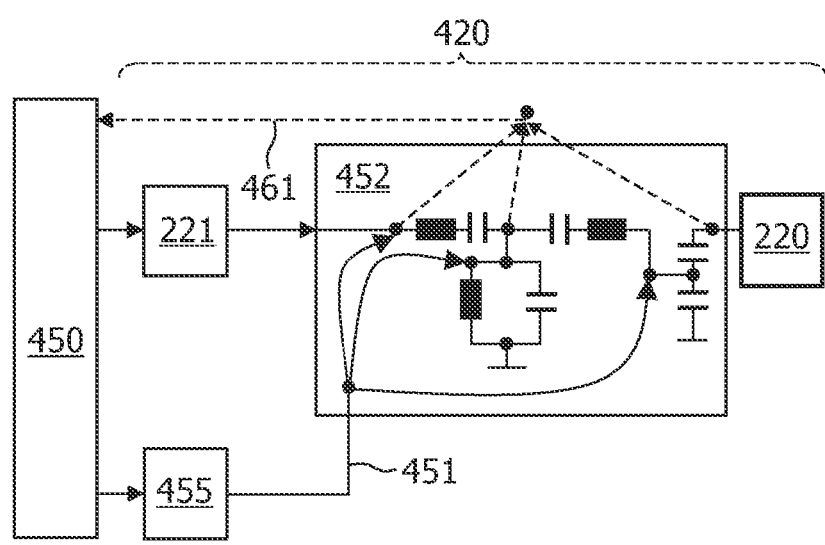

FIG. 10 schematically represents an embodiments of a drive signal chain.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Figure 1:
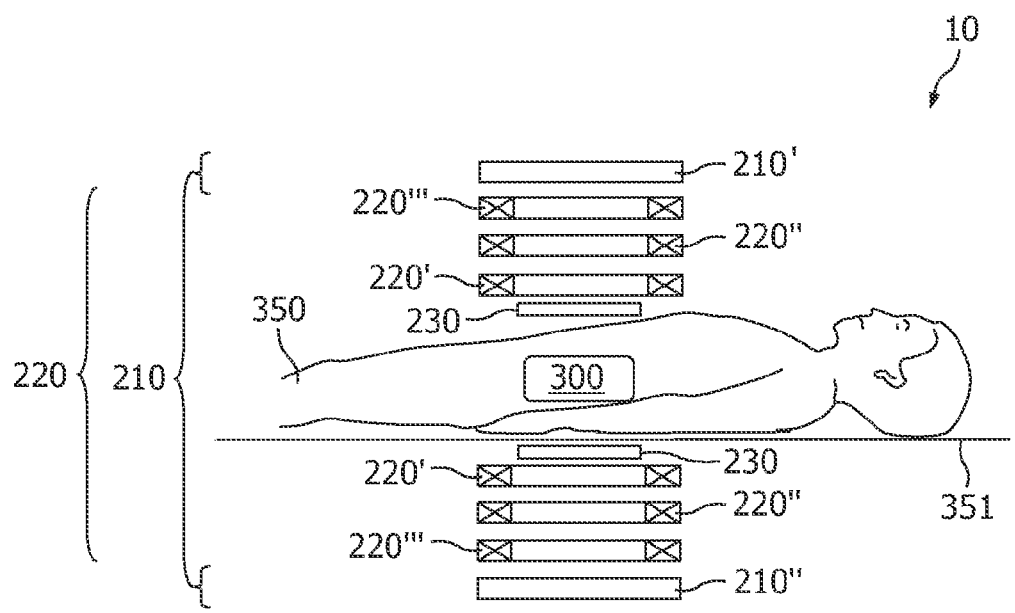
FIG. 1 illustrates an arrangement according to the present invention for carrying out the method according to the present invention.

In FIG. 1, an arbitrary object to be examined by means of an arrangement 10 according to the present invention is shown. The reference numeral 350 in FIG. 1 denotes an object, in this case a human or animal patient, who is arranged on a patient table, only part of the top of which is shown. Prior to the application of the method according to the present invention, magnetic particles 100 (not shown in FIG. 1) are arranged in a region of action 300 of the inventive arrangement 10. Especially prior to a therapeutical and/or diagnostical treatment of, for example, a tumor, the magnetic particles 100 are positioned in the region of action 300, e.g. by means of a liquid (not shown) comprising the magnetic particles 100 which is injected into the body of the patient 350.

Figure 2:
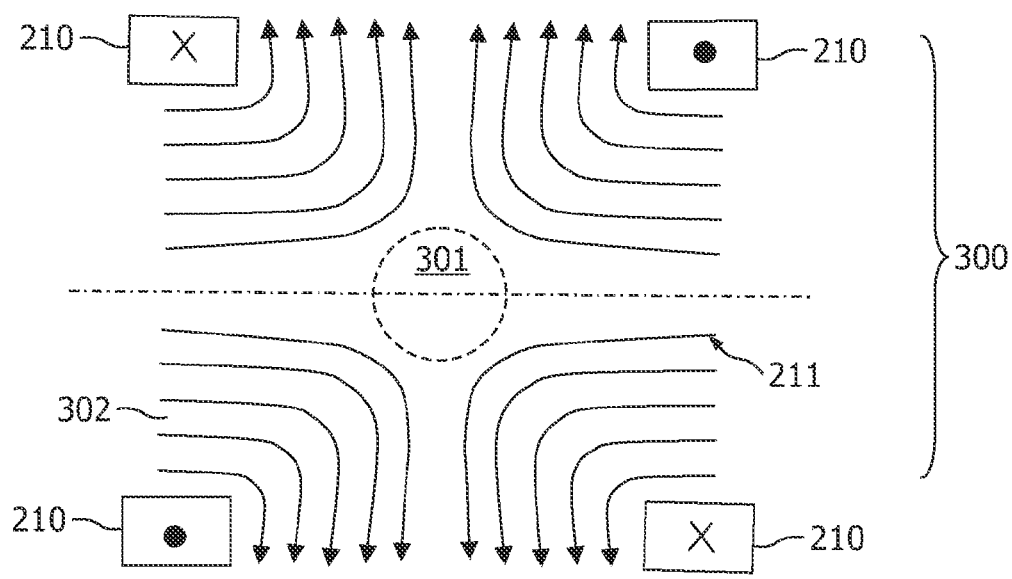
FIG. 2 illustrates an example of the field line pattern produced by an arrangement according to the present invention

As an example of an embodiment of the present invention, an arrangement 10 is shown in FIG. 2 comprising a plurality of coils forming a selection means 210 whose range defines the region of action 300 which is also called the region of treatment 300. For example, the selection means 210 is arranged above and below the patient 350 or above and below the table top. For example, the selection means 210 comprise a first pair of coils 210', 210", each comprising two identically constructed windings 210' and 210" which are arranged coaxially above and below the patient 350 and which are traversed by equal currents, especially in opposed directions. The first coil pair 210', 210" together are called selection means 210 in the following. Preferably, direct currents are used in this case. The selection means 210 generate a magnetic selection field 211 which is in general a gradient magnetic field which is represented in FIG. 2 by the field lines. It has a substantially constant gradient in the direction of the (e.g. vertical) axis of the coil pair of the selection means 210 and reaches the value zero in a point on this axis. Starting from this field-free point (not individually shown in FIG. 2), the field strength of the magnetic selection field 211 increases in all three spatial directions as the distance increases from the field-free point. In a first sub-zone 301 or region 301 which is denoted by a dashed line around the field-free point the field strength is so small that the magnetization of particles 100 present in that first sub-zone 301 is not saturated, whereas the magnetization of particles 100 present in a second sub-zone 302 (outside the region 301) is in a state of saturation. The field-free point or first sub-zone 301 of the region of action 300 is preferably a spatially coherent area; it may also be a punctiform area or else a line or a flat area. In the second sub-zone 302 (i.e. in the residual part of the region of action 300 outside of the first sub-zone 301) the magnetic field strength is sufficiently strong to keep the particles 100 in a state of saturation. By changing the position of the two sub-zones 301, 302 within the region of action 300, the (overall) magnetization in the region of action 300 changes. By measuring the magnetization in the region of action 300 or a physical parameter influenced by the magnetization, information about the spatial distribution of the magnetic particles in the region of action can be obtained. In order to change the relative spatial position of the two sub-zones 301, 302 in the region of action 300, a further magnetic field, the so-called magnetic drive field 221, is superposed to the selection field 211 in the region of action 300 or at least in a part of the region of action 300.

Figure 3:
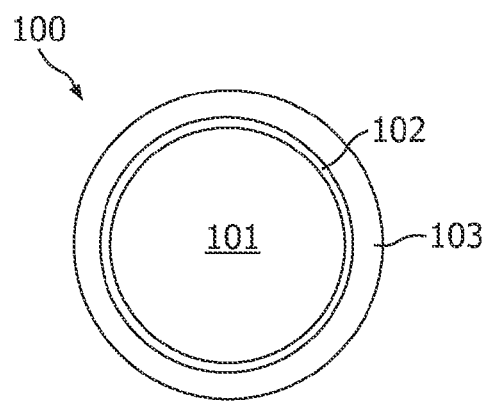
FIG. 3 illustrates an enlarged view of a magnetic particle present in the region of action.

FIG. 3 shows an example of a magnetic particle 100 of the kind used together with an arrangement 10 of the present invention. It comprises for example a spherical substrate 101, for example, of glass which is provided with a soft-magnetic layer 102 which has a thickness of, for example, 5 nm and consists, for example, of an iron-nickel alloy (for example, Permalloy). This layer may be covered, for example, by means of a coating layer 103 which protects the particle 100 against chemically and/or physically aggressive environments, e.g. acids. The magnetic field strength of the magnetic selection field 211 required for the saturation of the magnetization of such particles 100 is dependent on various parameters, e.g. the diameter of the particles 100, the used magnetic material for the magnetic layer 102 and other parameters.

In the case of e.g. a diameter of 10 µm, a magnetic field of approximately 800 A/m (corresponding approximately to a flux density of 1 mT) is then required, whereas in the case of a diameter of 100 µm a magnetic field of 80 A/m suffices. Even smaller values are obtained when a coating 102 of a material having a lower saturation magnetization is chosen or when the thickness of the layer 102 is reduced.

For further details of the preferred magnetic particles 100, the corresponding parts of DE 10151778 are hereby incorporated by reference, especially paragraphs 16 to 20 and paragraphs 57 to 61 of EP 1304542 A2 claiming the priority of DE 10151778.

The size of the first sub-zone 301 is dependent on the one hand on the strength of the gradient of the magnetic selection field 211 and on the other hand on the field strength of the magnetic field required for saturation. For a sufficient saturation of the magnetic particles 100 at a magnetic field strength of 80 A/m and a gradient (in a given space direction) of the field strength of the magnetic selection field 211 amounting to 160 $10^3$ A/m2, the first sub-zone 301 in which the magnetization of the particles 100 is not saturated has dimensions of about 1 mm (in the given space direction).

When a further magnetic field—in the following called a magnetic drive field 221 is superposed on the magnetic selection field 210 (or gradient magnetic field 210) in the region of action 300, the first sub-zone 301 is shifted relative to the second sub-zone 302 in the direction of this magnetic drive field 221; the extent of this shift increases as the strength of the magnetic drive field 221 increases. When the superposed magnetic drive field 221 is variable in time, the position of the first sub-zone 301 varies accordingly in time and in space. It is advantageous to receive or to detect signals from the magnetic particles 100 located in the first sub-zone 301 in another frequency band (shifted to higher frequencies) than the frequency band of the magnetic drive field 221 variations. This is possible because frequency components of higher harmonics of the magnetic drive field 221 frequency occur due to a change in magnetization of the magnetic particles 100 in the region of action 300 as a result of the non-linearity of the magnetization characteristics.

In order to generate these magnetic drive fields 221 for any given direction in space, there are provided three further coil pairs, namely a second coil pair 220', a third coil pair 220" and a fourth coil pair 220'" which together are called drive means 220 in the following. For example, the second coil pair 220' generates a component of the magnetic drive field 221 which extends in the direction of the coil axis of the first coil pair 210', 210" or the selection means 210, i.e. for example vertically. To this end the windings of the second coil pair 220' are traversed by equal currents in the same direction. The effect that can be achieved by means of the second coil pair 220' can in principle also be achieved by the superposition of currents in the same direction on the opposed, equal currents in the first coil pair 210', 210", so that the current decreases in one coil and increases in the other coil. However, and especially for the purpose of a signal interpretation with a higher signal to noise ratio, it may be advantageous when the temporally constant (or quasi constant) selection field 211 (also called gradient magnetic field) and the temporally variable vertical magnetic drive field are generated by separate coil pairs of the selection means 210 and of the drive means 220.

The two further coil pairs 220", 220'" are provided in order to generate components of the magnetic drive field 221 which extend in a different direction in space, e.g. horizontally in the longitudinal direction of the region of action 300 (or the patient 350) and in a direction perpendicular thereto. If third and fourth coil pairs 220", 220'" of the Helmholtz type (like the coil pairs for the selection means 210 and the drive means 220) were used for this purpose, these coil pairs would have to be arranged to the left and the right of the region of treatment or in front of and behind this region, respectively. This would affect the accessibility of the region of action 300 or the region of treatment 300. Therefore, the third and/or fourth magnetic coil pairs or coils 220", 220'" are also arranged above and below the region of action 300 and, therefore, their winding configuration must be different from that of the second coil pair 220'. Coils of this kind, however, are known from the field of magnetic resonance apparatus with open magnets (open MRI) in which an radio frequency (RF) coil pair is situated above and below the region of treatment, said RF coil pair being capable of generating a horizontal, temporally variable magnetic field. Therefore, the construction of such coils need not be further elaborated herein.

The arrangement 10 according to the present invention further comprise receiving means 230 that are only schematically shown in FIG. 1. The receiving means 230 usually comprise coils that are able to detect the signals induced by magnetization pattern of the magnetic particles 100 in the region of action 300. Coils of this kind, however, are known from the field of magnetic resonance apparatus in which e.g. a radio frequency (RF) coil pair is situated around the region of action 300 in order to have a signal to noise ratio as high as possible. Therefore, the construction of such coils need not be further elaborated herein.

In an alternative embodiment for the selection means 210 shown in FIG. 1, permanent magnets (not shown) can be used to generate the gradient magnetic selection field 211. In the space between two poles of such (opposing) permanent magnets (not shown) there is formed a magnetic field which is similar to that of FIG. 2, that is, when the opposing poles have the same polarity. In another alternative embodiment of the arrangement according to the present invention, the selection means 210 comprise both at least one permanent magnet and at least one coil 210', 210" as depicted in FIG. 2.

The frequency ranges usually used for or in the different components of the selection means 210, drive means 220 and receiving means 230 are roughly as follows: The magnetic field generated by the selection means 210 does either not vary at all over the time or the variation is comparably slow, preferably between approximately 1 Hz and approximately 100 Hz. The magnetic field generated by the drive means 220 varies preferably between approximately 25 kHz and approximately 100 kHz. The magnetic field variations that the receiving means are supposed to be sensitive are preferably in a frequency range of approximately 50 kHz to approximately 10 MHz.

Figure 4A:
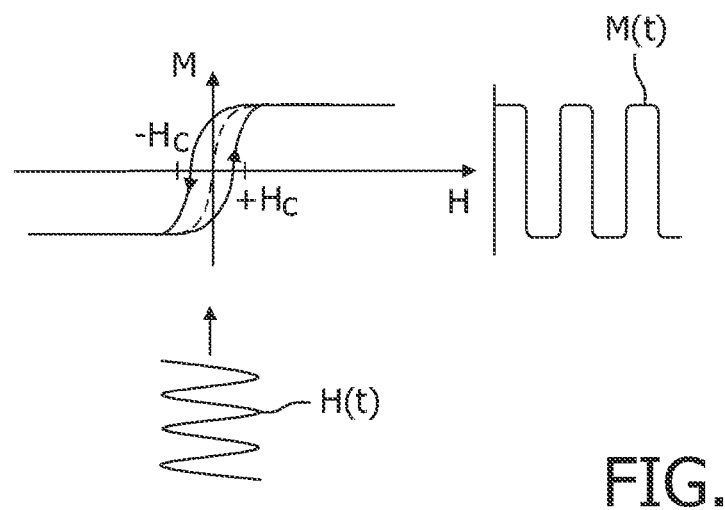
FIGS. 4a and 4b illustrate the magnetization characteristics of such particles.
Figure 4B:
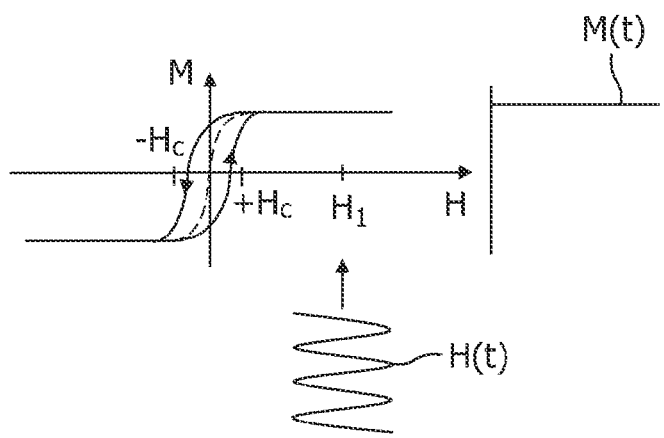

FIGS. 4a and 4b show the magnetization characteristic, that is, the variation of the magnetization M of a particle 100 (not shown in FIGS. 4a and 4b) as a function of the field strength H at the location of that particle 100, in a dispersion with such particles. It appears that the magnetization M no longer changes beyond a field strength $+H_c$ and below a field strength $-H_c$, which means that a saturated magnetization is reached. The magnetization M is not saturated between the values $+H_c$ and $-H_c$.

FIG. 4a illustrates the effect of a sinusoidal magnetic field H(t) at the location of the particle 100 where the absolute values of the resulting sinusoidal magnetic field H(t) (i.e. "seen by the particle 100") are lower than the magnetic field strength required to magnetically saturate the particle 100, i.e. in the case where no further magnetic field is active. The magnetization of the particle 100 or particles 100 for this condition reciprocates between its saturation values at the rhythm of the frequency of the magnetic field H(t). The resultant variation in time of the magnetization is denoted by the reference M(t) on the right hand side of FIG. 4a. It appears that the magnetization also changes periodically and that the magnetization of such a particle is periodically reversed.

The dashed part of the line at the centre of the curve denotes the approximate mean variation of the magnetization M(t) as a function of the field strength of the sinusoidal magnetic field H(t). As a deviation from this centre line, the magnetization extends slightly to the right when the magnetic field H increases from $-H_c$ to $+H_c$ and slightly to the left when the magnetic field H decreases from $+H_c$ to $-H_c$. This known effect is called a hysteresis effect which underlies a mechanism for the generation of heat. The hysteresis surface area which is formed between the paths of the curve and whose shape and size are dependent on the material, is a measure for the generation of heat upon variation of the magnetization.

FIG. 4b shows the effect of a sinusoidal magnetic field H(t) on which a static magnetic field $H_1$ is superposed. Because the magnetization is in the saturated state, it is practically not influenced by the sinusoidal magnetic field H(t). The magnetization M(t) remains constant in time at this area. Consequently, the magnetic field H(t) does not cause a change of the state of the magnetization.

Figure 5:
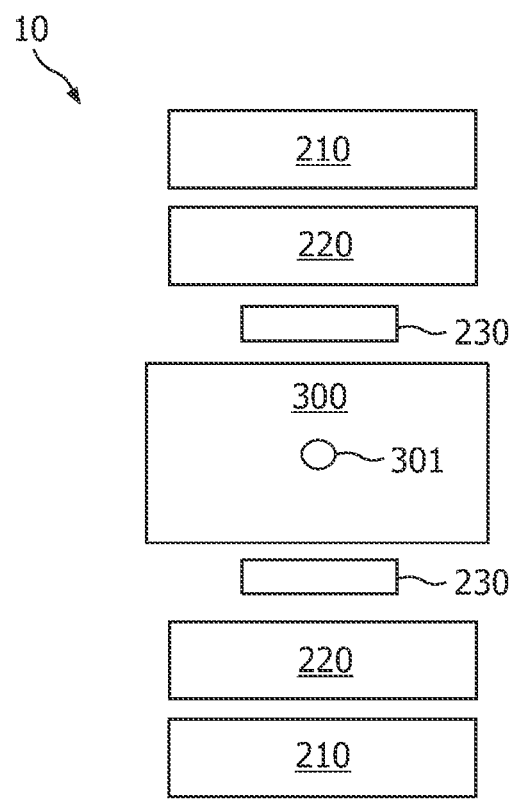
FIG. 5 illustrates schematically an arrangement 10 according to the present invention.

FIG. 5 schematically represents an arrangement 10 according to the present invention where the selection means 210, the drive means 220 and the receiving means 230 are depicted schematically in relation to a schematical representation of the region of action 300 and the first sub-zone 301 (containing the field-free point). Furthermore, the arrangement 10 comprises signal generation means (not depicted in FIG. 5) which serve to actuate the selection means 210 and the drive means 220, and signal processing means (not depicted in FIG. 5) which serve to detect or to record signals generated in the receiving means 230. The signal generation means and the signal processing means are at least partly depicted in greater detail in FIGS. 6 to 10

In FIGS. 6, 7 and 9, schematical representations of different embodiments of an arrangement 10 according to the present invention is shown. In these Figures, the arrangement 10 is shown comprising the drive means 220 and the receiving means 230 as well as the region of action 300. For the sake of simplicity, the selection means 210 are not depicted. Furthermore, the arrangement 10 comprises a drive signal chain 420 comprising the components used in order to generate and to process the drive signal finally fed to the drive means 220. Furthermore, the arrangement 10 comprises a detection signal chain 430 comprising the components used in order to process the detection signal generated in the receiving means 230. The drive signal chain comprise e.g. a drive signal generator 421 and further components like amplifiers, filters and the like which are represented by reference sign 422. The detection signal chain 430 comprises a detection signal processor 432 where all the detection signals are processed. The detection signal processor 432 preferably also comprises one or a plurality of amplifiers and one or a plurality of filters suitable for processing the detection signals. The inventive arrangement 10 further comprises a compensation controller 450. The compensation controller 450 generates a compensation signal 451 which is fed either to the drive signal chain 420 (FIG. 9) or to the detection signal chain 430 (FIGS. 6 and 7). According to the present invention, it is also possible (but not depicted) to feed the compensation signal 451 to both the drive signal chain 420 and to the detection signal chain 430. The compensation signal 451 is fed to the drive signal chain 420 and/or to the detection signal chain 430 by means of a coupling means 452. The coupling can be realized by means of capacitive coupling and/or resistive coupling and/or inductive coupling. The compensation signal 451 is generated by the compensation controller 450 by means of a feedback signal 461 derived from the drive signal chain 420 and/or from the detection signal chain 430.

According to preferred embodiments of the present invention (especially variants of the first embodiment), the compensation signal 451 is generated solely by means of passive components that have a very linear behavior but still give a certain flexibility in the control of the drive signal chain 420 and/or of the detection signal chain 430. Examples of such passive components are e.g. capacitors and/or coils or solenoids. In a very preferred embodiment, such passive components are only switched on or off by means of the compensation controller 450 in order to provide a suitable compensation to the drive signal chain 420 and/or to the detection signal chain 430. For different compensation scenarios, different passive elements like capacitors or coils are provided in the compensation controller 450. Usually, a part of these passive elements are switched on and a part are switched off. Thereby, a stepwise activation or passivation of the passive components are possible. The use of variable (continuously variable) passive components, e.g. variable capacitances, is also possible according to this preferred embodiment of the present invention. The use of active components like amplifiers and/or phase shifters is also possible together with the passive components. The problem using such active components is that they add to the compensation signal further unwanted harmonics such that further filter elements are potentially needed.

According to further preferred embodiments of the present invention (especially variants of the second and third embodiment), the compensation signal 451 is at least partially generated by active components such that a filtering needs to be applied before the coupling of the compensation signal 451 to the drive signal chain 420 and/or to the detection signal chain 430. As explained with the first embodiment, the compensation controller 450 can either be provided integrated with a drive signal generator 421 (only depicted in FIG. 6) or provide an independent unit. In this last variant of such an embodiment, it is possible that the compensation controller 450 measures the drive signal at the receiving means and estimates thereof the compensation signal 451.

In FIG. 6, the first embodiment according to the present invention is shown where the compensation signal 451 is fed to the detection signal chain 430. The feedback signal 461 can be derived from the drive signal chain 420 by means of a first branching means 462. Additionally or alternatively, the feedback signal 461 can be derived from the detection signal chain 430 by means of a second branching means 462'. In the first embodiment, the feedback signal 461 (also called reference signal) continuously provides information if the compensation of the complete drive signal chain 420 (including the drive means 220) and the compensation of the detection signal chain 430 is correct. The electronics of the compensation controller 450 provides preferably a shifting of the phase and an adjustment of the amplitude of the reference signals (i.e. either the electronics signals from the drive means 220 or the uncompensated signals from the receiving means 230 or both of them) and couples these changes to the detection signal chain 430 as a compensation signal 451. This is preferably done by passive components only. The coupling of the compensation signal 451 to the detection signal chain 430 is done in a way that only little noise is added to the high frequency components of the receiving means 230.

In FIGS. 7 and 8, the second embodiment according to the present invention is shown where the compensation signal 451 is also fed to the detection signal chain 430. In the second embodiment, the compensation controller 450 not only generates the compensation signal 451 but also generates the drive signal, i.e. the compensation controller 450 comprises the drive signal generator (not depicted in FIG. 7). Especially digital signal generation is realized which allows for more degrees of freedom.

The compensation signal 451 is also generated by the compensation controller 450. The coupling of the compensation signal 451 to the detection signal chain 430 can be done, e.g., by a transformer (inductive coupling) inside the coupling means 452, i.e. similar as when using a (stationary and/or moveable) compensation coil as part of the receiving means 230. This is shown in FIG. 8 where the detection signal chain 430 is depicted with an enlarged view of one possible coupling scenario (inductive coupling) inside the coupling means 452. The coupling means can also provide a capacitive bypass.

According to a variant of the second embodiment, it is possible that after the generation of the compensation signal 451, this signal travels trough a compensation signal chain 454 in order to be filtered and/or amplified and/or modified or corrected in a further way. This is done, e.g., to reduce undesired frequency components and is similar to the treatment of the signal inside the drive signal chain 420.

The feedback signal 461 is derived from the detection signal chain 430, especially the detection signal processor 432. From the feedback signal 461 derived from the detection signal chain 430 in a situation where the inventive arrangement is in a calibration mode operation, it is possible to generate the compensation signal 451 by means of measuring—in the calibration mode—the unwanted frequency components in the detection signal when a plurality of predefined (small) frequency and/or phase variations (called calibration variations) of the compensation signal 451 are applied. From the measurements of the effects of these comparably small calibration variations and by supposing a linear theory of the relationship between the calibration variations and the measured effects in the detection signal, it is possible to calculate the compensation signal, e.g. by inverting the transfer function.

In FIGS. 9 and 10, the third embodiment according to the present invention is shown where the compensation signal 451 is fed to the drive signal chain 420. Also in the third embodiment, the compensation controller 450 generates the drive signal, i.e. the compensation controller 450 comprises the drive signal generator (not depicted in FIG. 9). Especially digital signal generation is realized which allows for more degrees of freedom. The compensation signal 451 is subjected to a broad band signal chain 455 (as a special embodiment of a compensation signal chain 454). The compensation signal 451 is coupled or fed to the drive signal chain 420 after having passed the broad band signal chain 455. This is done in a way that the higher harmonics in the signal of the drive signal chain 420 are precisely compensated. The feeding or coupling point is preferably not directly after the amplifier (reference sign 422) of the drive signal chain 420 as in that case the needed power for the broad band signal chain 455 would be comparably high. According to variants of the third embodiment of the present invention, different coupling points are possible, which is depicted in greater detail in FIG. 10 where the drive signal chain 420 is depicted. In FIG. 10 different analog filter elements are used at the coupling means 452. Especially resistive coupling is used to couple the compensation signal 451 to the drive signal chain 420. Three different coupling points for the compensation signal 451 are shown as alternatives. According to further variants of the third embodiment of the present invention, the point of the coupling is preferably chosen such that at least one final passive filter stage is provided after the point of coupling (in the direction towards the drive means 220). This has the advantage that the performance of the inventive arrangement and especially the performance of the compensation is not limited by the precision of the feedback.

According to variants of the third embodiment of the present invention, the calibration feedback loop can either be realized in a continuous (or dynamic) manner or by means of a calibration mode. In both variants of the inventive arrangement, the feedback signal 461 is derived—at least indirectly—from the drive signal chain 420 such that the higher harmonics can be measured therein. In the calibration mode, the inventive arrangement is e.g. provided without a sample inside the arrangement and at different power levels and frequencies of the drive signal, the higher harmonics are measured. According to the present invention, this can be done using different measuring points as origins for the feedback signal 461. Different examples of such measuring points are depicted in FIG. 10. It is thereby possible to provide measurements of the deviations from the ideal drive signals. These deviations measured in the calibration mode (i.e. preferably without a sample inside the arrangement 10) are called the calibration variations. From the calibration variations, the compensation signal 451 is generated such that the calibration variations are as low as possible.

Alternatively according to the third embodiment of the present invention and contrary to the calibration mode, it is possible that the feedback signal 461 is provided in a feedback loop by means of an additional receiving means 465, i.e. especially an additional receiving coil. The additional receiving coil is preferably provided with a low sensitivity to the sample near the sample position.

The invention claimed is:

1. An arrangement for influencing and/or detecting magnetic particles in a region of action, wherein the arrangement comprises:
    a generator configured to generate a magnetic selection field having a pattern in space of its magnetic field strength such that a first sub-zone having a low magnetic field strength and a second sub-zone having a higher magnetic field strength are formed in the region of action;
    a driver configured to change a position in space of the two sub-zones in the region of action by a magnetic drive field so that the magnetization of the magnetic particles changes locally, the arrangement comprising a drive signal chain;
    a receiver configured to acquire detection signals, which detection signals depend on the magnetization in the region of action, wherein the magnetization is influenced by the change in the position in space of the first sub-zone and second sub-zone, the arrangement comprising a detection signal chain; and
    a compensation controller configured to provide a compensation signal to the drive signal chain and/or to the detection signal chain by at least one of a resistive coupling and an inductive coupling.

2. The arrangement according to claim 1, wherein the compensation signal is coupled to the drive signal chain and/or to the detection signal chain by a capacitive coupling.

3. The arrangement according to claim 1, wherein the compensation signal is filtered prior to being coupled to the drive signal chain and/or to the detection signal chain.

4. The arrangement according to claim 1, wherein the compensation controller is provided with a feedback signal from the drive signal chain and/or from the detection signal chain.

5. An arrangement for influencing and/or detecting magnetic particles in a region of action, wherein the arrangement comprises:
- a generator configured to generate a magnetic selection field having a pattern in space of its magnetic field strength such that a first sub-zone having a low magnetic field strength and a second sub-zone having a higher magnetic field strength are formed in the region of action;
- a driver configured to change a position in space of the two sub-zones in the region of action by a magnetic drive field so that the magnetization of the magnetic particles changes locally, the arrangement comprising a drive signal chain;
- a receiver configured to acquire detection signals, which detection signals depend on the magnetization in the region of action, wherein the magnetization is influenced by the change in the position in space of the first sub-zone and second sub-zone, the arrangement comprising a detection signal chain; and
- a compensation controller configured to provide a compensation signal to the drive signal chain and/or to the detection signal chain by a coupler,
- wherein the compensation controller is provided with a feedback signal from the drive signal chain and/or from the detection signal chain, and
- wherein the feedback signal is generated by an additional receiver.

6. An arrangement for influencing and/or detecting magnetic particles in a region of action, wherein the arrangement comprises:
- a generator configured to generate a magnetic selection field having a pattern in space of its magnetic field strength such that a first sub-zone having a low magnetic field strength and a second sub-zone having a higher magnetic field strength are formed in the region of action;
- a driver configured to change a position in space of the two sub-zones in the region of action by a magnetic drive field so that the magnetization of the magnetic particles changes locally, the arrangement comprising a drive signal chain;
- a receiver configured to acquire detection signals, which detection signals depend on the magnetization in the region of action, wherein the magnetization is influenced by the change in the position in space of the first sub-zone and second sub-zone, the arrangement comprising a detection signal chain; and
- a compensation controller configured to provide a compensation signal to the drive signal chain and/or to the detection signal chain by a coupler,
- wherein the compensation controller is provided with a feedback signal from the drive signal chain and/or from the detection signal chain, and
- wherein the feedback signal is generated using measuring points at the coupler.

7. The arrangement according to claim 6, wherein the arrangement comprises compensation signal chain and/or a broad band signal chain.

8. The arrangement according to claim 1, wherein the compensation controller is controlled by a computer.

9. A method for influencing and/or detecting magnetic particles in a region of action, wherein the method comprises the acts of:
- generating a magnetic selection field having a pattern in space of its magnetic field strength such that a first sub-zone having a low magnetic field strength and a second sub-zone having a higher magnetic field strength are formed in the region of action;
- changing the position in space of the two sub-zones in the region of action by a magnetic drive field formed by drive signals so that the magnetization of the magnetic particles changes locally;
- acquiring detection signals, wherein the detection signals depend on the magnetization in the region of action, wherein the magnetization is influenced by the change in the position in space of the first sub-zone and second sub-zone,
- compensating the drive signals and/or the detection signals a compensation signal coupled to the drive signals and/or coupled to the detection signals;
- wherein the compensation signal is generated by:
- measuring calibration variations in the drive signal and/or in the detection signals or applying calibration variations of the compensation signal to the drive signals and/or to the detection signals, and
- computing the compensation signal.

10. A method for calibrating an arrangement for influencing and/or detecting magnetic particles in a region of action, wherein the method comprises the acts of:
- generating a magnetic selection field having a pattern in space of its magnetic field strength such that a first sub-zone having a low magnetic field strength and a second sub-zone having a higher magnetic field strength are formed in the region of action;
- changing a position in space of the two sub-zones in the region of action by a magnetic drive field formed by drive signals;
- acquiring detection signals, wherein the detection signals depend on the magnetic drive field and/or on a magnetization of the magnetic particles in the region of action, and wherein the magnetization is influenced by the change in the position in space of the first sub-zone and second sub-zone;
- generating a compensation signal coupled to the drive signals and/or coupled to the detection signals, wherein the compensation signal is generated by:
- measuring calibration variations in the drive signal and/or in the detection signals or applying calibration variations of the compensation signal to the drive signals and/or to the detection signals, and
- computing the compensation signal.

11. The method according to claim 10, wherein the calibration variations of the compensation signal are provided as phase shift variations and/or amplitude variations.

12. The method according to claim 10, further comprising the act of
- changing the position in space of the two sub-zones in the region of action by the magnetic drive field so that the magnetization of the magnetic particles changes locally.

13. The method according to claim 10, wherein the compensation signal is computed by applying linear theory calculations.

14. The arrangement according to claim 1, wherein the compensation signal is coupled to the drive signal chain and/or to the detection signal chain by a capacitive bypass.

* * * * *